United States Patent [19]

Crosby

[11] 4,261,916
[45] Apr. 14, 1981

[54] SULPH(ON)ATION PROCESS

[75] Inventor: Michael J. Crosby, Cumbria, England

[73] Assignee: Albright & Wilson Limited, Warley, England

[21] Appl. No.: 959,093

[22] Filed: Nov. 9, 1978

Related U.S. Application Data

[63] Continuation of Ser. No. 686,432, May 14, 1976, abandoned.

[30] Foreign Application Priority Data

May 15, 1975 [GB] United Kingdom ............... 20568/75

[51] Int. Cl.$^3$ ............... C07C 141/02; C07C 143/02; C07C 143/24; C07C 141/04
[52] U.S. Cl. ............... 260/458 R; 260/400; 260/401; 260/457; 260/459 R; 260/504 R; 260/505 E; 260/505 S; 260/505 C; 260/513 T
[58] Field of Search ............ 260/505 S, 505 E, 459 R, 260/458 R, 400, 401, 457, 504 R, 513 T, 505 C

[56] References Cited

U.S. PATENT DOCUMENTS

| | | | |
|---|---|---|---|
| 2,828,331 | 3/1958 | Marisic | 260/505 S |
| 3,956,372 | 5/1976 | Coleman et al. | 260/505 S |

OTHER PUBLICATIONS

Gilbert, "Sulfonation and Related Reactions", (1956), pp. 66–69.

Primary Examiner—Alan Siegel
Attorney, Agent, or Firm—Frishauf, Holtz, Goodman & Woodward

[57] ABSTRACT

An orifice plate mixer for mixing 2 fluids has an axial orifice perpendicular to the plate through which bore a first fluid passes and a port in the internal wall of the orifice through which the second fluid passes. The mixer can impart high turbulence to the first fluid and is especially useful in the sulph(on)ation of organic feedstocks with sulphur trioxide in a recycle loop reactor having said mixer, a pump, a heat exchanger and inlet and outlet for feedstock and reaction products.

22 Claims, 4 Drawing Figures

SULPH(ON)ATION PROCESS

This is a continuation of application Ser. No. 686,432 filed May 14, 1976 now abandoned.

The invention relates to an orifice plate mixer and methods of using it.

There are many mixing operations in which two or more fluids are to be mixed as quickly as possible to avoid local high concentrations of one of the fluids in contact with the other fluid. Examples of such operations are sulphonation, sulphation or halogenation reactions in which the organic reactant is sensitive to high concentrations of the sulphonating/sulphating-/halogenating reagent. Among known mixers are orifice plate mixers, which are described for use in such reactions in e.g. British Patent Specification No. 975914. In this patent specification the sulphonating-/sulphating reagent, which is a sulphur trioxide/air mixture, is caused to flow in an axially directed pipe passing through the axial orifice of the orifice plate mixer with emission of the reagent into the turbulent area downstream of the mixer.

We have now found that an improved mixing action can be obtained if one of the fluids is introduced through a port located in the internal wall of the axial orifice of the plate.

Our invention provides a turbulent flow plate mixer for mixing at least two fluids which comprises an orifice which is substantially perpendicular to the plate and a port in the internal wall of the orifice, the orifice being for passage of the first fluid and the port being for passage of the second fluid. The orifice constitutes a bore through the plate with the port a passage in the wall of the bore.

This configuration gives a high degree of turbulence and mixing because the fluid passing through an orifice in the plate experiences a relatively high pressure drop and has a high Reynolds Number at the point of mixing the two fluids; this is true even if the diameter of the orifice is relatively large, the length of the orifice is relatively small, being only the thickness of the plate, thus allowing substantial vortex formation and turbulence downstream of the orifice as well as in the orifice.

These characteristics distinguish the turbulent flow plate mixer of the invention from Venturi tubes in which the pressure drop is minimized by providing a convergent entry to and divergent exit from the tube, both of small angle, the velocity is maximized and the turbulence minimized by providing a comparatively small diameter of bore; and the length of the tube is comparatively large.

The duct leading the second fluid to the port in the wall of the orifice may be drilled through the thickness of the plate, conveniently in a radial direction. It is not, however, essential that the port be flush with the internal wall, and it is possible to introduce a pipe or collar projecting beyond the wall in a radial, upstream or downstream direction.

The plate may be of circular, square or rectangular cross section with the orifice preferably at its centre; the centre of the port is preferably about equally spaced from the ends of the orifice, e.g. at a distance of 40-60% of the length of the orifice from the end of the orifice.

Preferably the mixer comprises an integral plate in which an axial bore or orifice and at least one radial duct or port have been fabricated, e.g. by drilling, the orifice having the port or ports in its internal wall.

As mentioned above, the configuration of the mixer according to the invention can give a high Reynolds number to a fluid passing through the orifice. The dimensions should be such, in relation to the mass density of the first fluid, its viscosity and linear velocity in the orifice, that the Reynolds number in the orifice is greater than the minimum for turbulent flow, i.e. 2000, but preferably greater than 3000, e.g. 3000-20,000, preferably 4500-15,000 and especially 10,000-15,000 when the first fluid is a liquid and the second fluid is soluble therein or reacts therewith. The greater the diameter of the orifice for a constant volume of fluid through the orifice the smaller the Reynolds number and the pressure drop across the plate, so that the choice of diameter is a compromise between the desire for a high Reynolds number giving maximum turbulence and avoidance of a high pressure drop requiring maximum power input. In general the design will be a compromise of the conflicting requirements of high throughput and Reynolds number with a reasonable applied pump pressure on the one hand and a high pressure drop across the plate on the other.

The diameter of the orifice in relation to the thickness of the plate, i.e. the length of the orifice is relatively high, generally of at least 0.5:1, e.g. 1:1 to 50:1, preferably 1:1 to 20:1, especially 1.5:1 to 10:1. It will be understood that references to a "plate" herein include a fabricated construction made up of two thin plates joined together, the space between them being such as to accommodate a feed pipe to the port. The "orifice" then takes the form of a short length of pipe between the two thin plates.

If desired there may be more than one port e.g. 2-4 ports in the internal wall at the orifice. These may be used to introduce the same or different fluids.

Preferably the first fluid is an organic feedstock which is to be reacted with the second fluid in a manner to minimise over-reaction. Thus the second fluid can be a sulphonating, sulphating or halogenating reagent where over-reaction can produce discolouration of the product or production of a product having more than the desired number of substituent groups. This over-reaction can also occur in the reaction of hydroxylic organic feedstocks with an alkylene oxide, e.g. ethylene oxide where it is desired to add only certain number of alkylene oxide units to the feedstock and hence minimize the spread of the number of alkylene oxide units in the product. While the fluids can be liquid or gaseous, the first fluid is preferably liquid, while the second fluid may be liquid or gaseous. The fluids are usually mutually miscible ether because of mutual solution or reaction.

The present invention also provides a method of mixing at least two fluids which comprises passing a first fluid through an orifice which is in a plate and substantially perpendicular to the plate, and passing a second fluid into the first fluid through a port in an internal wall of the orifice.

The method of mixing of the invention will be described hereafter with reference to the sulphonating-/sulphating of organic feed stocks with sulphur trioxide in a recycle loop system, but it is equally applicable to other reactions in which over-reaction is undesirable whether or not a recycle loop system is adopted, e.g. in an in line system with mixing of reactants in the mixer and subsequent collection of the reaction products.

In the preferred process the mixing plate used in the present invention forms part of a recycle loop comprising the plate, a pump, a heat exchanger, a line joining these together in a loop, and entry lines into the loop for the feedstock and the sulphur trioxide, and a take off line for the product. The entry line for the feedstock is before the mixer plate in the direction of flow in the loop and the entry line for the sulphur trioxide is into the mixer. Thus the second fluid is the sulphur trioxide as gas or liquid and the first fluid is a mixture of organic feedstock and its sulph(on)ated product. Preferably the fluids are mixed in the mixer before they reach the pump, i.e. the mixer is on the inlet side of the pump, and preferably the fluids pass through the mixer, pump and heat exchanger before the take off line is reached.

When a sulph(on)atable organic compound, e.g. an aromatic compound such as benzene or a fatty alcohol such as lauryl alcohol is sulph(on)ated by sulphur trioxide, there is a considerable evolution of heat, which, if associated with local high concentrations of sulphur trioxide in the reaction mixture, may give rise to a heavily discoloured reaction product.

In this Specification the terms "sulph(on)ated", "sulph(on)atable" and "sulph(on)ation" means sulphonated, sulphonatable and sulphonation, or sulphated, sulphatable and sulphation, depending on the nature of the compound reacted; thus aromatic hydrocarbons are sulphonated, but fatty alcohols are sulphated. In order to produce light coloured sulph(on)ated products, such as aromatic sulphonic acid reaction products for use, e.g. as surface active agents or hydrotropes or fatty alcohol sulphate reaction products for use, e.g. as surface active agents, it is usual to moderate the effects of the heat of reaction by diluting the sulphur trioxide, either with an inert gas, e.g. to a 5% concentration in dry air, or with an inert liquid diluent, e.g. a chlorinated hydrocarbon or liquid sulphur dioxide. The need for the gaseous or liquid diluent introduces problems of purification of the diluent before the reaction and removal thereafter and problems in use. Thus gaseous diluents have to be dried before use and separated from the reaction product after the reaction without entrainment of product, unreacted sulph(on)atable compound and/or liquid diluent. The presence of gaseous diluents in the liquid reaction medium means that they are more difficult to pump than liquid phases only. Liquid diluents have to be separated from the reaction product. It has also been proposed to use the sulphur trioxide gas as such and undiluted but under externally applied reduced pressure. It is known to react the sulph(on)atable compound with liquid sulphur trioxide in a complicated apparatus in which the sulphur trioxide is directed at an organic compound present on the surface of at least four moving impeller blades which are close to heat transfer surfaces. The reacting mixture of organic compound and sulphur trioxide is sheared between the impeller blade and the heat transfer surface to reduce the temperature. Finally, it is known to sulph(on)ate sulph(on)atable compounds with a sulphur trioxide/air mixture in a loop reactor with removal of one fifth to one thirtieth of the reaction product and recycle of the rest. It is suggested in a further document that undiluted gaseous sulphur trioxide could be used in a continuous loop process but no details are given.

The mixer of the invention can be used to prepare a sulph(on)ated product by a process with undiluted liquid or gaseous sulphur trioxide in a simple apparatus with a loop in which the organic feedstock is diluted with its recycled sulph(on)ated reaction product, contact between organic feedstock and sulphur trioxide occurs under conditions of turbulent flow in the mixer and the amount of recycle is very high. The process has the advantage of requiring no diluent for the sulphur trioxide and in the case of alkyl benzene feedstocks often gives light coloured products.

The present invention particularly provides a process for sulph(on)ating a sulph(on)atable organic feedstock, which is preferably an aromatic compound or a fatty alcohol of 8–18 carbon atoms, which comprises passing a reactant liquid comprising the organic feedstock and its sulph(on)ation derivative as the first fluid through a first orifice of a plate, the orifice being substantially perpendicular to the plate, and having a port in the internal wall of the orifice, and passing undiluted sulphur trioxide as second fluid in liquid or gaseous form through said port, the apparent Reynolds number of the reactant liquid in the orifice at the point of meeting the port being in the range 2000–20,000 and the liquid being in a condition of turbulent flow at the point of contact of sulphur trioxide and liquid and thereafter in the zone of reaction of sulphur trioxide and liquid, the mixing of the sulphur trioxide and feedstock producing a reaction mixture, cooling the reaction mixture before and/or after removing a portion of the reaction mixture as sulph(on)ated product, the weight ratio of reaction mixture removed to the remainder of reaction mixture being in the range 1:40 to 1:2000, adding further organic feedstock to the remainder of the reaction mixture to compensate for that removed as product and to reconstitute the reactant liquid and recycling it for contact with more sulphur trioxide.

The compounds which may be sulphonated in the process of the invention, include aromatic compounds of 6–36 carbon atoms free from groups unstable under the reaction conditions, e.g. free amino groups. Examples are benzene and alkyl benzenes having 1–3 alkyl groups, each of 1–15 carbon atoms, such as alkyl benzenes with 1–3 alkyl groups, each of 1 to 5, especially 1 to 3 carbon atoms, e.g. toluene and the 3 isomers of xylene, and monoalkyl benzenes in which the alkyl group contains 8–15 carbon atoms, e.g. dodecyl benzenes, such as benzene with a linear dodecyl or propylene tetramer side chain. The aromatic compound may have one or two substituents which are halogen atoms, such as chlorine or bromine (as in chloro toluenes), hydroxyl groups (as in phenol) or carboxylic groups (as in benzoic acid); the aromatic compound may have one nitro or one sulphonic acid substituent. The total number of substituents in any benzene ring is usually not more than 3. The naphthalene equivalents of the above compounds, e.g. naphthalene itself may also be sulphonated. Other classes of sulphonatable organic feedstocks are olefins, e.g. those of 8–20 carbon atoms, such as dodec-1-ene, hexadec-1-ene and octadec-1-ene, or randon unsaturated hexadecene or vinylidene olefins, and fatty acids, e.g. those of 8–20 carbon atoms such as lauric and stearic acids, as well as olefinic acids, e.g. of 3–20 carbon atoms, preferably 4–18 carbon atoms such as maleic, fumaric and oleic acids.

Examples of sulphatable organic feedstocks are alcohols, preferably fatty ones of 8–20 carbon atoms, such as lauryl, cetyl and stearyl alcohols and mixtures thereof, including mixtures such as are commercially available with a larger proportion of one of these alcohols and smaller amounts of other alcohols. The reaction products of these fatty alcohols with ethylene oxide or propylene oxide which usually contain 1–10 of structural units derived fron the oxide may be sulphated. Alkyl phenols with, e.g. 1-12 carbon atoms in the alkyl group, and the reaction products of 1 mole of them with, e.g. 1-10 moles of ethylene oxide or propylene oxide, fatty acid alkanol amides, e.g. with 8-18 carbon atoms in the fatty acid part, e.g. that derived from lauric acid and 2-12 carbon atoms in the alkanolamide part, e.g. that derived from mono or di or tri ethanolamine, and the reaction products of 1 mole of the fatty acid alkanolamides with e.g. 1-10 moles of ethylene oxide or propylene oxide may also be sulphated.

Preferably however, the sulph(on)atable compound is benzene or an alkyl benzene as defined above or a fatty alcohol. The sulphur trioxide is preferably in gaseous form.

The sulph(on)ated products may be used in detergent compositions.

The sulphur trioxide and organic feedstock are contacted in the mixer when the liquid containing the feedstock is in a condition of turbulent flow, preferably with an apparent Reynolds Number of at least 2,000, e.g. at least 3000, usually 3000-18,000, preferably 4500-15,000 and especially 10,000 to 15,000. The Reynolds Number can be greater than 18,000 but the higher values become progressively uneconomic. The apparent Reynolds Number is calculated on the assumption that there is no gas phase present, i.e. in the case of the use of gaseous $SO_3$ its volume is neglected.

The turbulent flow is achieved by use of the mixer and also in the loop circuit through which the liquid flows there is a pump; the requirement for turbulent flow necessitates a pump operating at a high pumping rate. The turbulent flow occurs in the mixer and in the reaction zone wherever unreacted sulphur trioxide contacts feedstock (or sulph(on)ated derivatives thereof) and reacts with it. Most pumps and heat exchangers for cooling the reaction mixture keep turbulent a liquid fed thereinto in a state of turbulent flow. Fixed pressure pumps, e.g. centrifugal pumps are preferred though any other type of pump capable of a high pumping rate may be used. colour sulphonates from alkly benzenes can best be produced if the liquid mixes with the sulphur trioxide before passing through the pump rather than afterwards, i.e. the mixer is at the inlet side of the pump rather than the outlet side. The recycle loop system also contains a heat exchanger as cooler, and inlet for feedstocks and outlet for reaction mixture. Preferably the cooler is between the mixer and outlet in the direction of liquid flow. Thus preferably the sulph(on)ation occurs in a recycle loop reactor through which is pumped the reaction liquid and mixture, the reactor having in the direction of flow of the reaction mixture and liquid, an inlet for feedstock, a mixer giving turbulent flow into which sulphur trioxide, preferably in gaseous form is passed, a pump, a heat exchanger as cooler and an outlet for reaction mixture. The reaction liquid and mixture are preferably in a state of turbulent flow in the mixer, pump and heat exchanger and may be in that state throughout the loop. The sulphur trioxide and feedstock are passed into the loop continuously and the sulph(on)ation product is removed continuously.

The temperature of the liquid as it enters the mixer before reaction with sulphur trioxide is primarily governed by the need to control the viscosity of the liquid, the lower limit being that to maintain a viscosity such that there is turbulent flow, the upper limit being preferably 150° C., and pressure being placed on the system if necessary to stop volatilization of the organic compound at the liquid temperature. Preferably the temperature of the liquid is 0°-80° C., and especially 20°-60° C. The use of high temperatures may tend to give greater discolouration in the sulphonated products than occurs at lower temperatures, but the viscosity of the reaction liquid is lower at high temperature, making for higher turbulence for the same power input to the pump or the same turbulence with a lower power input. A balance is drawn between the opposing factors. During the reaction, heat is evolved and the maximum temperature of the effluent reaction mixture is preferably 150° C.; the usual temperature is 25°-65° C. Generally, there is no externally applied vacuum on the loop system in which the reaction mixture and reaction liquid are kept. The loop system is usually maintained with an external pressure of at least substantially atmospheric, e.g. up to 18 atmospheres and preferably about atmospheric pressure, i.e. there is preferably no externally applied pressure or vacuum.

The liquid which is reacted with the sulphur trioxide may contain an inert liquid diluent, such as a chlorinated aliphatic hydrocarbon, e.g. carbon tetrachloride. Such a diluent may be desirable when the reaction product is so high melting or of such viscosity that the temperature needed to recycle the reaction product when liquid and give turbulent flow in the mixer would be high enough to result in undue discolouration and/or formation of other byproducts. Examples of such reaction products are those from naphthalene compounds, alkanolamides, alkoxylated derivatives thereof and alkoxylated alcohols and phenols. However, preferably the inert diluent is absent so that no step of separating the diluent after the reaction is needed and the final product is substantially the sulph(on)ated products or the main liquid contaminant is unreacted feedstock which can be separated and recycled for reuse.

After the reaction has occurred, the reaction mixture is cooled, usually to a temperature the same as the input temperature of the recycle liquid before reaction. The reaction is exothermic the heat of reaction being absorbed in the bulk of the circulating liquid as a heat sink. The cooling is preferably such as to give a maximum temperature difference of the liquid in different parts of the loop of 50° C. especially a maximum difference of 10° C. The cooling may take place in one or more stages with the reaction mixture being passed through one or more heat exchangers. Usually the portion of reaction mixture is withdrawn as reaction product after at least partial cooling of the reaction liquid and the remainder is mixed with fresh organic feedstock to compensate for the organic feedstock reacted and removed, and to bring the content of feedstock in the mixture back to the value desired for the input feed into the reaction with sulphur trioxide. The liquid with the content of organic sulph(on)atable compound restored in this fashion is then recycled for further reaction with sulphur trioxide. Alternatively but less preferred, the reaction mixture may be cooled after the portion is withdrawn, the cooling occurring before or after the fresh feedstock is added.

The portion of reaction mixture taken out of the system constitutes a fortieth to a two thousandth of the weight of the remainder of the reaction mixture recycled, i.e. a recycle ratio of 40:1 to 2,000:1, preferably 100:1 to 1,000:1, e.g. 100:1 to 700:1 and especially 150-650:1, e.g. 150-350:1 such as 150-275:1.

The amount of the feedstock in the reaction liquid depends on the nature of the feedstock, the desired composition of the product removed from the system, and the recycle ratio.

When the feedstock is degraded by a substantial excess of sulphur trioxide and when any unreacted feedstock is difficult to separate from the sulph(on)ated product, as is true for most aliphatic feedstocks and also for example, with dodecyl benzene, the molar ratio of $SO_3$ to feedstock is usually 0.9:1 to 1.1:1, e.g. 0.9:1 to 1.05:1, preferably 0.93:1 to 1.05:1, especially 0.93:1 to 1.0:1. In these cases the molar ratio of the amount of feedstock in the reaction liquid to be contacted with $SO_3$ to the amount of sulph(on)ated derivative in that liquid is preferably 0.01:99.99 to 5:95 and especially about 0.1:99.9 to 3:97. When the feedstock to be sulphonated is not easily degraded by an excess of $SO_3$, the molar ratio of $SO_3$ to feedstock may be greater than 1:1, e.g. in the range 0.9:1 to 2:1 or if unreacted feedstock is more easily separated from the reaction product, as with lower alkyl benzenes then the molar ratio of $SO_3$ to feedstock may be 0.1:1 to 1:1 e.g. 0.5:1 to 0.95:1. Molar ratios of $SO_3$ to feedstock greater than 1.2:1 are used when disulphonation, e.g. of aromatic hydrocarbons is desired. The composition of the liquid to be reacted with $SO_3$ can vary over a wide range. When the unreacted feedstock level in the product removed from the system is to be kept low so that the reaction mixture is substantially free (i.e. less than 2%) of unreacted feedstock, the molar ratio of feedstock to sulphonated derivative may be 0.01:99.99 to 10:90, preferably 0.01:99.99 to 5:95, e.g. 0.1:99.9 to 3:97. When the product is to contain a substantial amount of unreacted volatile feedstock the molar ratio of feedstock to sulphonated derivative may be 5:95 to 90:10, e.g. 15:85 to 90:10. The latter proportions may often be advantageous if the product is to be purified for removal of sulphones obtained with aromatic hydrocarbon feedstocks, because the crude product can be treated with water and the aqueous sulphonic acid layer separated from an organic layer comprising unreacted feedstock and water insoluble impurities, such as the sulphones. The sulphur trioxide:-feedstock molar ratio is determined by the desired composition of the product, as well as the nature of the feedstock.

The product removed from the system can be used as such or converted to the corresponding salt by treatment with a base and/or purified to remove impurities.

Thus in the case of reaction of the aromatic compounds with sulphur trioxide in a molar ratio of less than 1:1.2 the liquid removed from the system comprises any unreacted aromatic compound and sulphonated compounds which are primarily the mono sulphonic acids of the aromatic compounds and inert liquid diluent (if used in the reaction) and also may contain small amounts of disulphonic acids, sulphuric acid and/or sulphones. When the molar ratio of sulphur trioxide to aromatic feedstock is greater than 1.2:1 the liquid removed from the system comprises sulphonated compounds which are disulphonic acids and monosulphonic acids and inert liquid diluent (if used in the reaction), and may also contain small amounts of unreacted aromatic compound, sulphuric acid and/or sulphones. The sulphonic acids may be sold as such, or after treatment with a base to form an aqueous phase comprising a solution of a sulphonate salt. The base may be an aqueous solution of an alkali metal hydroxide, carbonate or bicarbonate, e.g. sodium hydroxide or sodium carbonate or ammonia or an organic amine, such as a trialkyl amine or dialkyl amine, each with 1 to 4 carbon atoms in each alkyl group, e.g. dimethylamine or an alkylolamine, e.g. ethanolamine. Alternatively the liquid is treated with water, optionally after adding a hydrocarbon solvent eg benzene, toluene, xylene or paraffin to cause separation into an aqueous phase containing the sulphonic acids and an organic phase containing unreacted aromatic compound and sulphone (and the hydrocarbon added). There is no need to add further hydrocarbon if the product removed from the system contains a substantial amount of unreacted volatile aromatic compound, as mentioned above or water immiscible liquid diluent. The aqueous sulphonic acid can be used as such or converted into a salt as described above. The treatment of the crude liquid with the aqueous solution of base can also be followed by separation of the organic phase as described above. Traces of residual organic feedstock and hydrocarbons can be removed from the sulphonic acid or salt product by stripping e.g. under vacuum.

In order to minimize the production of sulphones in the sulphonation reaction, when the feedstock is benzene or benzene substituted by at least one alkyl chain of 1–5 carbon atoms, it is preferred to carry out the reaction in the presence of a sulphone inhibitor.

The sulphone inhibitor is usually added with the feedstock if it is soluble therein, but otherwise it is added separately to the reaction liquid usually before the addition of the sulphur trioxide. Amounts of inhibitor of up to 10% (by weight based on the weight of the sulphonated product) may be used, e.g. up to 5%, preferably 0.5–5% especially 1–5%. The inhibitors may be oxygenated compounds, nitrogenous compounds or metal salts. The class of oxygenated compounds includes those described in our British Patent Specification No. 1306226 such as cyclic ethers, e.g. of 4–8 carbon atoms such as dioxan or tetrahydrofuran, dialkyl ethers, e.g. of 1–4 carbon atoms in each alkyl group such as diethyl ether, dialkyl ketones, e.g. of 3–7 carbon atoms such as acetone and methyl ethyl ketone cycloaliphatic ketones such as cyclo-hexanone, carboxylic acids, e.g. of 2–6 carbon atoms such as acetic or propionic acids, esters of these carboxylic acids, e.g. with alkanols of 1 to 6 carbon atoms such as ethyl acetate, and anhydrides of those carboxylic acids such as acetic anhydride; acetic acid and acetic anhydride are preferred. The class of nitrogenous compounds includes those described in our British Pat. No. 1304514 and includes mono amines e.g. of formula $R_3N$ where each R, which may be the same or different, is hydrogen, alkyl e.g. of 1 to 6 carbon atoms, cycloalkyl, e.g. of 5–7 carbon atoms or aryl (preferably aromatic hydrocarbyl), e.g. of 6–12 carbon atoms, such as ammonia, di and tri alkyl amines such as triethyl amine and diisopropylamine, primary aromatic and cycloalkyl amines such as aniline and cyclohexylamine; diamines and triamines, e.g. alkylene diamines of 2–6 carbon atoms such as ethylene diamine and alkylene triamines of 4–10 carbon atoms such as diethylene triamine:heterocyclic amines such as pyridine, quinoline and isoquinoline; carboxylic acid amides e.g. the amide from any primary or secondary amine mentioned above preferably ammonia or dimethyl amine and a carboxylic acid of 1 to 4 carbon atoms such as carbonic, formic and acetic acids, preferably urea, dimethyl formamide and dimethyl acetamide; amine salts, where the amine part can be based on any of the amines mentioned above, e.g. ammonium, and the acid part is from an inorganic acid such as hydrochloric, sulphuric or phosphoric acid, or an organic, sulphonic or carboxylic acid such as aromatic hydrocarbyl or alkyl sulphonic acids such as xylene-, or toluene-, benzene-, or methane sulphonic acids. The metal salts includes alkali metal salts of organic or inorganic acids, which are the alkali metal salt equivalents of the amine salts mentioned above.

When the sulphonated aromatic product is wanted in its acid form, the inhibitor is preferably an oxygenated compound, e.g. acetic acid or acetic anhydride because the other inhibitors introduce often undesirable compounds into the acid, e.g. ammonium salts. When the sulphonated aromatic product is wanted in its salt form, the presence of ammonium salts or production of ammonia as byproducts from, e.g. urea is of no consequence because the neutralization of the free acid product liberates the amine or ammonia, which can be separated from the salt.

The feedstock or the sulphone inhibitor (if the latter is not added with the feedstock) may be mixed with up to 300% (by weight of inhibitor), preferably 20-170% of water or the water may be added separately to the reaction liquid. The water appears to act as an auxiliary sulphone inhibitor but may result in a higher percentage of free sulphuric acid in the reaction product, which may be desirable in certain applications. Water added alone is a poor sulphone inhibitor and increases the content of free sulphuric acid in the reaction product considerably. Examples of useful combinations of inhibitor and water are water and carboxylic acids, esters or anhydrides, e.g. water and acetic acid, acetic anhydride or ethyl acetate.

When the organic feedstock sulphated is a fatty alcohol, the reaction mixture removed from the system comprises unreacted alcohol and the desired mono alkyl sulphate (and inert diluent if present) together sometimes with the di alkyl sulphate ester. The mixture is usually treated with an aqueous solution of a base, e.g. one as described above to form an aqueous phase comprising an aqueous solution of a sulphate salt. The amount of base is at least sufficient to neutralize the reaction product. Similar operations may be carried out when the feedstock is any of the other sulphatable compounds.

The sulph(on)ated products of our invention can be treated by any of the known techniques used to produce saleable materials. For example, in the case of the sulphonation of olefins having 8-20 carbon atoms it is necessary to include a process step which results in the hydrolysis of the sultones formed in the reaction. Another example is that in the case of the sulphonation of dodecyl benzene it may be desirable to add small amounts of water to the sulphonic acid product in order to prevent the colour of the sulphonic acid darkening on storage and to prevent pH drift of salts produced from it. This procedure is disclosed in British Pat. No. 804349. If desired one of the process steps in the treatment of the products of the invention can be bleaching by any suitable means.

In a most preferred process, the sulph(on)ation is carried out in a recycle loop reactor having in the direction of flow of reaction liquid and mixture, an inlet for feedstock, an orifice plate mixer and inlet for sulphur trioxide together in a mixer comprising a plate having an orifice, which is substantially perpendicular to said plate and a port in the internal wall of the orifice, the ratio of the diameter of the orifice to the thickness of the plate being 1:1 to 20:1, a pump, a heat exchanger as cooler and an outlet for said reaction mixture, the sulph(on)ation reaction being carried out with undiluted gaseous sulphur trioxide and a reaction liquid free of inert diluent at a temperature of 20°-80° C. under substantially no externally applied pressure or vacuum, the Reynolds Number at the point of mixing being 10,000-15,000, the recycle weight ratio of the reaction mixture removed to the recycled remainder being 150-350:1 preferably 150-275:1 and, when the feedstock is benzene or an alkyl benzene, the reaction liquid also contains a sulphone inhibitor in amount of 1-5% by weight of feedstock.

The mixer of the invention can be of simple construction and the condition for successful operation of mixing and reaction processes using it on a small scale, e.g. of at least 10 lb/hr total weight of sulphur trioxide and added feedstock can be scaled up easily for larger scale processes, e.g. at least 200 lb/hr.

The invention may be illustrated with reference to the accompanying drawings, in which.

Figure 1:
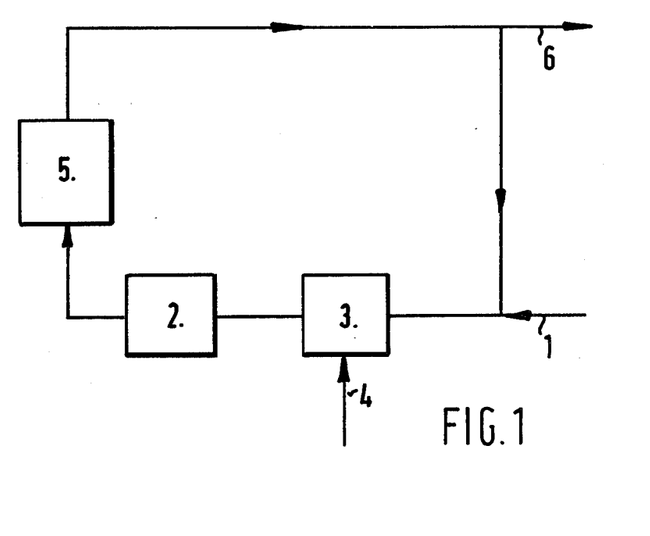
FIG. 1 represents a flow diagram of a preferred process, FIG. 2 a flow diagram of an alternative but less preferred process.
Figure 2:
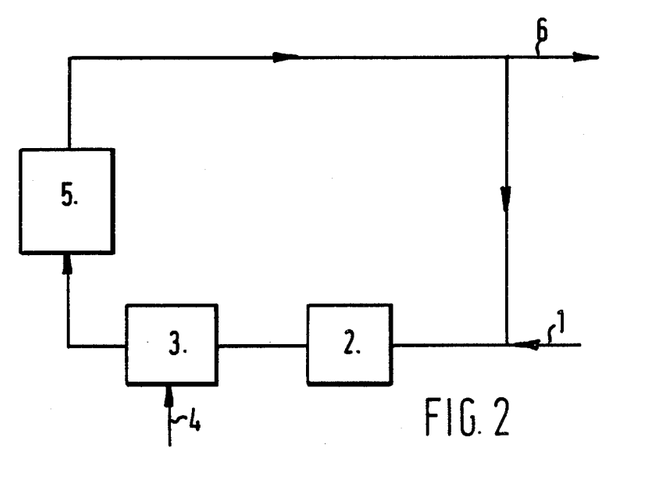

In FIGS. 1 and 2 of the drawings the loop has an input line 1, a pump 2, turbulent flow mixer 3, an input line 4 to mixer 3, a heat exchanger 5, and an output line 6.

In the operation of FIG. 1 the mixture of unreacted organic feedstock and sulph(on)ated organic feedstock (referred to hereafter as a "heel") is circulated round the loop by pump 2. Fresh organic feed stock is passed into the loop from line 1 and the mixture of it and the heel is rendered turbulent, so that the mixture is turbulent at the point in mixer 3 where sulphur trioxide enters the loop from line 4, the reaction mixture produced is drawn through pump 2 and pumped further round the loop through the heat exchanger 5; a very small portion of the reaction mixture is removed through line 6 and the remainder is recycled for contact with fresh organic feedstock from line 1. Alternatively the remainder of the small portion of the reaction mixture may be removed before passage through the heat exchanger.

The operation of FIG. 2 is similar, except that the pump 2 and mixer 3 are transposed.

Figure 3:
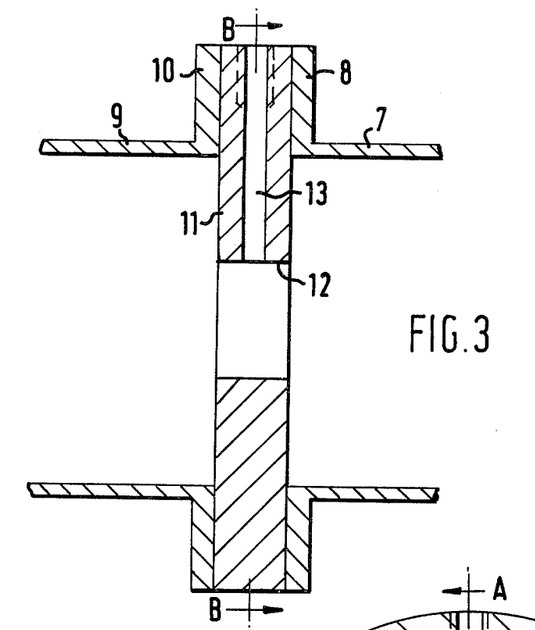
FIG. 3 represents a section through a mixer plate, and its associated pipework, the section being taken along the line AA of FIG. 4
Figure 4:
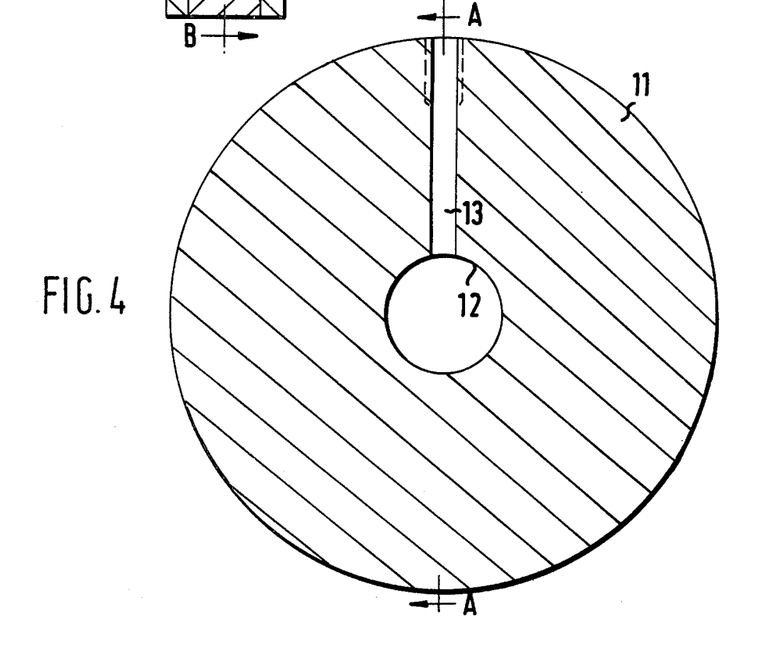
FIG. 4 represents a section along the line BB through the mixer plate of FIG. 3.

Turning now to FIGS. 3 and 4, conduit 17 with flange 8 is spaced from corresponding conduit 9 and flange 10 by a mixer plate 11 which has an axial orifice 12 at its centre. The ratio of the diameter of the axial orifice to the length of the orifice is particularly 1.63:1. From the middle of orifice 12 is disposed a radial secondary port 13, the external end of which has been drilled out for a short distance to receive a feedpipe (not shown).

In use a first fluid is passed through conduit 7 and thence through axial orifice 12, where it becomes turbulent and meets the second fluid, which has passed through secondary port 13. The turbulent mixture of first and second fluids then passes further into conduit 9. The mixer which is described with respect to FIGS. 3 and 4 may be used in sulph(on)ation processes, the flow diagrams for which are shown in FIGS. 1 and 2.

The invention is illustrated by the Examples set out in the following Tables.

The apparatus was as shown in FIG. 1.

The Table gives the approximate Reynolds Number at the point of mixing the SO₃ and the reaction liquid, the Number quoted being calculated on the assumption that there is no gas phase present. In Examples 1-3, the mixer was one of the invention as illustrated with reference to FIGS. 3 and 4 with a 0.87:1 ratio of diameter of orifice to plate thickness and in Example 4 the mixer was one of the invention as illustrated with reference to FIGS. 3 and 4 but modified with a 3.5:1 ratio of diameter of orifice to plate thickness.

The recycle ratio quoted is the weight ratio of the circulation rate to the rate of feeding the feedstock and SO₃ into the loop; the rate of input feed is the same as the rate of off take.

For Examples 1, 2 and 4 the reaction product taken from the loop at outlet 6 was analysed for total acidity (by titration with alkali, and expressed as % sulphuric acid), % free sulphuric acid, % sulphone, % free hydrocarbon and % disulphonic acids. The colour quoted was ten times the reading measured using an Eel Colorimeter with a Blue 303 filter on an aqueous solution of the reaction product, obtained by adding water to the reaction product to give a 65% by weight aqueous solution of sulphonic acid and separating unreacted hydrocarbon and any precipitate of sulphone.

For Example 3 the alcohol sulphated was a mixture of fatty alcohols in which $C_{12}$ and $C_{14}$ alcohols predominated, the mixture being that sold under the Trade Name "Laurex NC". The reaction product was neutralized with aqueous sodium hydroxide to yield a 28% aqueous solution, whose colour was measured as before. The neutralized reaction product was also analyzed for total surface active matter, sodium sulphate and free fatty matter (by ether extraction of the neutralized product)

I claim:
1. A method for sulph(on)ating a sulph(on)atable organic feedstock selected from the group consisting of benzene, alkylbenzenes having 1-3 alkyl groups each of 1-5 carbon atoms, alkylbenzenes containing 1 alkyl substituent of 8-15 carbon atoms, naphthalene and the alkylnaphthalene equivalents of said alkylbenzenes, olefins, fatty acids, olefinic acids, alcohols, alkylphenols, fatty acid alkanol amides, and condensates of alcohols, alkylphenols or fatty acid alkanol amides with ethylene oxide or propylene oxide, by reaction with sulphur trioxide in a turbulent flow plate mixer, said turbulent flow orifice plate mixer comprising a plate, means defining an orifice through said plate, said orifice being substantially perpendicular to said plate, an internal wall to said orifice, and means defining at least one port in said wall, comprising passing undiluted sulphur trioxide in liquid or gaseous form through said port into a reactant liquid free of inert liquid diluent comprising the organic feedstock and its sulph(on)ation derivative passing through said orifice to give a reaction mixture, the apparent Reynolds Number of the reactant liquid in said orifice at the point of meeting the port being 2000-20,000 and the liquid at the point of meeting the port and thereafter in the zone of reaction of the sulphur trioxide and the liquid being in a condition of turbulent flow, cooling the reaction mixture, removing a portion of the reaction mixture as sulph(on)ated product, the weight ratio of reaction mixture removed to the remainder of reaction mixture being in the range 1:100 to 1:700, and adding further organic feedstock to the remainder of the reaction mixture to compensate for that removed as product and to reconstitute said reactant liquid and recycling it to said orifice for contact with more sulphur trioxide.

| Example | Feedstock | Feedstock Feedrate (lbs/hr) | SO₃ Physical State | SO₃ Feedrate (lbs/hr) | Sulphone Inhibitor (Wt % of feedstock) | Circulation Rate Imp. Gal/hr | Circulation Rate approx. lb/hr | Recycle Ratio | Running Temperature °C. | Pressure Drop Across Plate (cms Hg) | Approx. Reynolds Number |
|---|---|---|---|---|---|---|---|---|---|---|---|
| 1 | Toluene | 44 | Vapour | 36 | Acetic acid (3.4%) | 1590 | 21,000 | 258:1 | 53-56 | 64.5 | 6,700 |
| 2 | Toluene | 50 | Vapour | 34.3 | Acetic acid (3.4%) | 1530 | 16,800 | 199:1 | 52-55 | 59.6 | 13,820 |
| 3 | "Laurex NC" Alcohol | 45 | Vapour | 18 | — | 1680 | 16,800 | 267:1 | 39-43 | 60.0 | 4,950 |
| 4 | Toluene | 212 | Vapour | 180 | Acetic Anhydride (1.75%) | 1200 | 235,000 | 600:1 | 50-55 | 41.0 | 12,040 |

The molar ratio SO₃:feedstock were:
Ex. 1 1:1.06
Ex. 2 1:1.27
Ex. 3 1:1.03
Ex. 4 1:1.20

| PRODUCT ANALYSIS | | | | | | |
|---|---|---|---|---|---|---|
| Example | % Total Acidity (as sulphuric acid) | Sulphuric Acid (%) | Sulphones (%) | Free Hydrocarbon (%) | Disulphonic Acid (%) | Colour (Eel B) |
| 1 | 27.8 | 1.6 | 2.6 | 3.8 | <0.1 | 5 |
| 2 | 25.3 | 1.7 | 3.9 | 13.0 | <0.1 | 4 |
| 4 | 27.7 | 1.8 | 4.8 | 3.9 | 0.5 | 8 |

| Example | % Active Matter | % Sodium Sulphate | % Free Fatty Matter | Colour (Eel B) |
|---|---|---|---|---|
| 3 | 27.0 | 0.37 | 0.58 | 6 |

2. A method according to claim 1 wherein the reaction mixture and reactant liquid are in a loop system maintained under no externally applied vacuum.

3. A method according to claim 1 wherein the apparent Reynolds Number of the reactant liquid in said orifice is 4,500–18,000.

4. A method according to claim 3 wherein the apparent Reynolds Number of the reactant liquid in said orifice is 10,000 to 15,000.

5. A method according to claim 1 wherein the sulphur trioxide is in gaseous form.

6. A method according to claim 1 wherein the ratio of the diameter of the orifice to the thickness of the plate is 1:1 to 10:1.

7. A method according to claim 1 wherein the reactant liquid and sulphur trioxide are contacted in said mixer at a temperature of 0°–80° C.

8. A method according to claim 1 wherein the molar ratio of sulphur trioxide to feedstock is such that the reaction mixture is substantially free of unreacted feedstock.

9. A method according to claim 1 which is carried out in a recycle loop reactor having in the direction of flow of the reaction liquid and mixture, an inlet for feedstock, said mixer giving turbulent flow to the reaction liquid, a pump, a heat exchanger as cooler and an outlet for reaction mixture.

10. A method according to claim 1 wherein said organic feedstock is benzene or an alkyl benzene having 1–3 alkyl groups each of 1 to 3 carbon atoms, or a fatty alcohol of 8–20 carbon atoms.

11. A process according to claim 1 wherein said organic feedstock is toluene or xylene.

12. A process according to claim 1 in which said organic feedstock is benzene or an alkyl benzene, wherein the reaction liquid also comprises a sulphone inhibitor in amount of up to 10% by weight based on the weight of the feedstock.

13. A process according to claim 12 wherein the inhibitor is acetic acid, acetic anhydride or an alkyl acetate with 1–6 carbon atoms in the alkyl group.

14. A process according to claim 12 wherein water is added to the reactant liquid in amounts of up to 300% by weight of the inhibitor.

15. A process according to claim 12 wherein the inhibitor is an amine or ammonium salt, amide or urea.

16. A method according to claim 1 wherein the portion of the sulphonated reaction mixture removed as product is treated with water to give an aqueous phase comprising an aqueous solution of a sulphonic acid.

17. A method according to claim 1 wherein the portion of the sulphonated or sulphated reaction mixture removed as product is treated with an aqueous solution of a base to give an aqueous phase comprising a solution of a sulphonate or sulphate salt.

18. A method according to claim 10, wherein the sulph(on)ation is carried out in a recycle loop reactor having in the direction of flow of reaction liquid and mixture, an inlet for feedstock, said turbulent flow plate mixer, having a ratio of the diameter of said orifice to the thickness of said plate of 1:1 to 20:1, a pump, a heat exchanger as cooler and an outlet for said reaction mixture, the sulph(on)ation reaction being carried out with undiluted gaseous sulphur trioxide and a reaction liquid free of inert diluent at a temperature of 20°–80° C. under substantially no externally applied pressure or vacuum, the Reynolds Number at the point of mixing being 10,000–15,000, the weight ratio of the reaction mixture removed as product to the recycled remainder being between 1:150 and 1:350.

19. A method according to claim 18, wherein said feedstock is benzene or an alkylbenzene, and wherein said reactant liquid also contains a sulphone inhibitor in an amount of 1–5% by weight of said organic feedstock.

20. A method according to claim 1, wherein said reaction mixture is cooled before removal of said product.

21. A method according to claim 1, wherein said reaction mixture is cooled after removal of said product.

22. A method according to claim 1, wherein said benzene compounds and naphthalene compounds contain one substituent selected from the group consisting of chlorine, bromine, hydroxyl, carboxyl, nitro, and sulphonic acid substituents, or two substituents selected from the group consisting of chlorine, bromine, hydroxyl, and carboxyl substituents.

* * * * *

UNITED STATES PATENT AND TRADEMARK OFFICE
CERTIFICATE OF CORRECTION

PATENT NO. : 4,261,916
DATED : April 14, 1981
INVENTOR(S) : Michael J. CROSBY

It is certified that error appears in the above—identified patent and that said Letters Patent is hereby corrected as shown below:

Column 4, line 55: change "randon" to --random--.

Column 4, line 68: change "fron" to --from--.

Column 5, line 40: before "colour", insert ---Light---.

Column 8, line 47: before "No. 1304514", insert --Specification--.

Column 9, line 55: after "Pat.", insert --Specification--.

Signed and Sealed this

Fifth Day of January 1982

[SEAL]

Attest:

GERALD J. MOSSINGHOFF

Attesting Officer      Commissioner of Patents and Trademarks